(12) United States Patent
Cantin et al.

(10) Patent No.: US 7,209,605 B2
(45) Date of Patent: Apr. 24, 2007

(54) PACKAGED OPTICAL SENSORS ON THE SIDE OF OPTICAL FIBERS

(75) Inventors: Daniel Cantin, Sainte-Foy (CA); Alain Cournoyer, Québec (CA); Marc Lévesque, Saint-Augustin-de-Desmaures (CA); Julie Fréchette, Sainte-Foy (CA); Sylvain Plante, Québec (CA)

(73) Assignee: Institut National d'Optique, Quebec (CA)

( * ) Notice: Subject to any disclaimer, the term of this patent is extended or adjusted under 35 U.S.C. 154(b) by 0 days.

(21) Appl. No.: 10/371,020

(22) Filed: Feb. 19, 2003

(65) Prior Publication Data
US 2003/0231818 A1    Dec. 18, 2003

(30) Foreign Application Priority Data
Feb. 20, 2002    (CA) .................................. 2372637

(51) Int. Cl.
*G02B 6/00* (2006.01)
*G02B 6/02* (2006.01)
*G02B 6/16* (2006.01)

(52) U.S. Cl. .................. 385/12; 385/13; 385/123; 385/125; 385/126

(58) Field of Classification Search ............ 385/12–13, 385/37, 141–145, 123; 250/227, 214, 227.14, 250/227.16–227.19, 227.23, 227.31–227.32, 250/573–577, 216; 350/96.34, 96.29; 374/130–131; 422/82.05–82.13; 356/39–42
See application file for complete search history.

(56) References Cited

U.S. PATENT DOCUMENTS

| | | | |
|---|---|---|---|
| 4,075,493 A | 2/1978 | Wickersheim | 250/461 R |
| 4,136,566 A | 1/1979 | Christensen | 73/355 |
| 4,215,275 A | 7/1980 | Wickersheim | 250/459 |
| 4,223,226 A | 9/1980 | Quick et al. | 250/458 |
| 4,245,507 A | 1/1981 | Samulski | 73/356 |
| 4,376,890 A | 3/1983 | Engstrom et al. | 250/227 |
| 4,387,954 A * | 6/1983 | Beasley | 385/30 |
| 4,409,476 A | 10/1983 | Lofgren et al. | 250/227 |

(Continued)

FOREIGN PATENT DOCUMENTS

| | | | |
|---|---|---|---|
| GB | 2184859 | | 7/1987 |
| GB | 2184859 A | * | 7/1987 |
| JP | 4-258744 | * | 9/1992 |
| JP | 7-328128 | * | 12/1995 |

OTHER PUBLICATIONS

Fiberguide Industries, Inc., Superguide PCS UV-VIS Fiber, Mar. 2002, Specification Features Section.*

(Continued)

*Primary Examiner*—Frank G. Font
*Assistant Examiner*—Ryan Lepisto
(74) *Attorney, Agent, or Firm*—Merchant & Gould P.C.

(57) ABSTRACT

The present invention concerns an optical sensor located on a preferred azimuthal portion of the side of an optical fiber. An optical fiber having two opposite ends, a core and a cladding and at least one sensing area is disclosed. Each of the sensing areas is located between the two opposite ends and each has a longitudinal, a radial and an azimuthal portion of the fiber that has been removed and replaced by a sensing material. The sensing collected light is thus representative of a parameter to be measured, such as temperature. Placing the sensing material in a lateral side portion of the fiber increases the sensitivity of the sensor, particularly when it comes to contact temperature measurement in vivo.

26 Claims, 7 Drawing Sheets

U.S. PATENT DOCUMENTS

| | | | | |
|---|---|---|---|---|
| 4,536,058 A | * | 8/1985 | Shaw et al. | 385/30 |
| 4,560,248 A | * | 12/1985 | Cramp et al. | 385/12 |
| 4,562,348 A | | 12/1985 | Brogårdh et al. | 250/231 R |
| 4,644,154 A | | 2/1987 | Brogårdh et al. | 250/227 |
| 4,710,623 A | * | 12/1987 | Lipson et al. | 250/227.28 |
| 4,729,668 A | | 3/1988 | Angel et al. | 374/161 |
| 4,752,115 A | * | 6/1988 | Murray et al. | 385/12 |
| 4,798,954 A | * | 1/1989 | Stevenson | 250/341.7 |
| 4,827,121 A | * | 5/1989 | Vidrine et al. | 356/451 |
| 4,880,972 A | | 11/1989 | Brogårdh et al. | 250/231 R |
| 4,883,354 A | | 11/1989 | Sun et al. | 356/128 |
| 4,889,407 A | * | 12/1989 | Markle et al. | 385/12 |
| 4,895,156 A | | 1/1990 | Schulze | 128/634 |
| 4,915,503 A | | 4/1990 | Pavlath | 356/460 |
| 4,986,671 A | | 1/1991 | Sun et al. | 374/131 |
| 5,028,395 A | * | 7/1991 | Sebille et al. | 422/82.06 |
| 5,052,820 A | * | 10/1991 | McGinniss et al. | 374/131 |
| 5,056,520 A | * | 10/1991 | Tomisaka et al. | 600/312 |
| 5,109,442 A | * | 4/1992 | Klainer et al. | 385/12 |
| 5,124,130 A | * | 6/1992 | Costello et al. | 422/82.06 |
| 5,127,405 A | | 7/1992 | Alcala et al. | 128/633 |
| 5,168,156 A | * | 12/1992 | Fischer et al. | 250/227.21 |
| 5,218,419 A | * | 6/1993 | Lipson et al. | 356/477 |
| 5,225,887 A | * | 7/1993 | Lipson et al. | 356/477 |
| 5,234,835 A | | 8/1993 | Nestor et al. | 436/11 |
| 5,244,636 A | * | 9/1993 | Walt et al. | 422/82.07 |
| 5,249,251 A | | 9/1993 | Egalon et al. | 385/12 |
| 5,253,037 A | * | 10/1993 | Klainer et al. | 356/133 |
| 5,298,645 A | | 3/1994 | Iyer et al. | 558/267 |
| 5,298,741 A | * | 3/1994 | Walt et al. | 250/227.23 |
| 5,311,013 A | | 5/1994 | Gutcheck et al. | 250/227.23 |
| 5,324,933 A | * | 6/1994 | Berkcan | 250/227.23 |
| 5,332,316 A | | 7/1994 | Kleinerman | 374/161 |
| 5,333,609 A | * | 8/1994 | Bedingham et al. | 600/339 |
| 5,335,305 A | * | 8/1994 | Kosa et al. | 385/147 |
| 5,351,268 A | | 9/1994 | Jensen et al. | 374/131 |
| 5,359,681 A | * | 10/1994 | Jorgenson et al. | 385/12 |
| 5,363,463 A | | 11/1994 | Kleinerman | 385/123 |
| 5,408,999 A | | 4/1995 | Singh et al. | 128/634 |
| 5,426,213 A | | 6/1995 | Iyer et al. | 560/222 |
| 5,525,800 A | * | 6/1996 | Sanghera et al. | 250/339.08 |
| 5,567,622 A | * | 10/1996 | Jaduszliwer et al. | 436/106 |
| 5,585,634 A | * | 12/1996 | Stevenson et al. | 250/339.11 |
| 5,633,494 A | * | 5/1997 | Danisch | 250/227.16 |
| 5,730,528 A | | 3/1998 | Allison et al. | 374/161 |
| 5,859,937 A | * | 1/1999 | Nomura | 385/12 |
| 5,864,641 A | * | 1/1999 | Murphy et al. | 385/12 |
| 5,871,449 A | | 2/1999 | Brown | 600/474 |
| 5,903,685 A | * | 5/1999 | Jones et al. | 385/12 |
| 5,935,075 A | | 8/1999 | Casscells et al. | 600/474 |
| 5,982,959 A | * | 11/1999 | Hopenfeld | 385/12 |
| 6,141,098 A | | 10/2000 | Sawatari et al. | 356/345 |
| 6,166,806 A | * | 12/2000 | Tjin | 356/336 |
| 6,188,812 B1 | * | 2/2001 | Kao et al. | 385/12 |
| 6,245,026 B1 | | 6/2001 | Campbell et al. | 600/549 |
| 6,328,932 B1 | * | 12/2001 | Carter et al. | 422/82.06 |
| 6,432,364 B1 | * | 8/2002 | Negami et al. | 422/82.11 |
| 6,846,286 B2 | * | 1/2005 | Suzuki et al. | 600/145 |
| 6,882,872 B2 | * | 4/2005 | Uchida et al. | 600/310 |
| 2002/0186748 A1 | | 12/2002 | Yates et al. | 374/161 |
| 2003/0052256 A1 | * | 3/2003 | Spirin et al. | 250/227.11 |
| 2004/0264901 A1 | * | 12/2004 | Tao et al. | 385/128 |

OTHER PUBLICATIONS

International Search Report from PCT/CA03/00235.*

Udd E., "An overview of Fiber-Optic Sensors", Review of Scientific Instruments, American Institute of Physics, pp. 4015-4030, vol. 66, No. 8, Aug. 1, 1995.*

Rogers A., "Distributed Optical-Fibre Sensing", Measurement Science and Technology, IOP Publishing, pp. R75-R99, vol. 10 No. 8, Aug. 1999.*

James T. Willerson MD et al. Specific Platelet Mediators and Unstable Coronary Artery Lesions; Experimental Evidence and Potential Clinical Implications. Point of View vol. 80, No. 1, Jul. 1989, pp. 198-205.

Ward Casscells et al., Thermal detection of cellular infiltrates in living atherosclerotic plaques: possible implications for plaque rupture and thrombosls. The Lancet vol. 347, May 25, 1996, pp. 1447-1449.

S.W. Allison, G. T. Gillies, Remote thermometry with thermographic phosphors: Instrumentation and applications; Rev. Sci. Instrum. 68 (7) Jul. 1997 pp. 2615-2650.

S.F. Collins, et al. Comparison of fluorescence-based temperature sensor schemes: Theoretical analysis and experimental validation; Journal of Applied Physics, vol. 84, No. 9, pp. 4649-4654.

V.C. Femicola et al., Investigations on exponential lifetime measurements for fluorescence thermometry; Review of Scientific Instruments p. 1.

Zhlyl Zhang et al., A novel signal processing scheme for a fluorescence based fiber-optic temperature sensor; Rev.Sci.Instrum.62 (7) Jul. 1991 pp. 1735-1742.

Kenneth A. Wickersheim et al. Fiberoptic Thermometry and its Applications; 1987 International Microwave Power Institute; pp. 349-358.

Khawar Gul et al., Coronary Thermosensor Basket Catheter with Thermographic Imaging Software for Thermal Detection of Vulnerable Atherosclerotic Plaques; 4 pages; Sep. 13, 2001.

P.R.N. Childs et al., Review of temperature measurement; Review of Scientific Instruments, vol. 71, No. 8, Aug. 2000, pp. 2959-2978.

Christodoulos Stefanadis, et al. Thermal Heterogeneity within Human Atherosclerotic coronary Arteries detected In Vivo; A new method of detection by application of a special Thermography Catheter, Circulation 1999—pp. 1965-1971.

Barry J. Prince et al., A readout Scheme Providing High Spatial Resolution for Distributed Fluorescent Sensors on Optical Fibers; Analytical Chemistry, vol. 73, No. 5, Mar. 1, 2001, pp. 1007-1015.

An Overview of Fiber-Optic Sensors, Review of Scientific Instruments, American Institute of Physics, New York, US vol. 66, No. 8, Aug. 1, 1995 pp. 4015-4030.

Distributed Optical-Fibre Sensing, A. Rogers, Measurement Science and technology, IOP Publishing, Bristol, GB, vol. 10, No. 8, Aug. 1999 pp. R75-R99.

Temperature Sensor Based on Etched Optical Fiber With a Metal Coating, J. Yan et al., International Journal of Infrared and Millimeter Waves, Plenum Publishing, New York, US, vol. 18, No. 7, Jul. 1, 1997 pp. 1423-1430.

Fiberoptic Temperature Sensors in the Medical Setting, Mei H. Sun et al., Selected Papers on optical fibers in medecine, SPIE Milestone Series, Bellingham, SPIE, US, vol. MS 11, 1990, pp. 304-310.

* cited by examiner

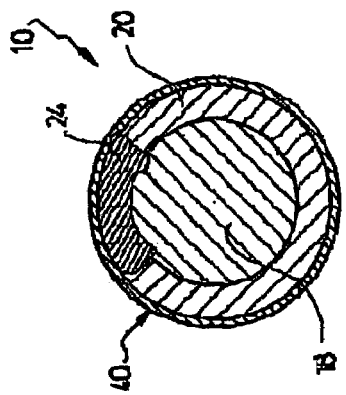
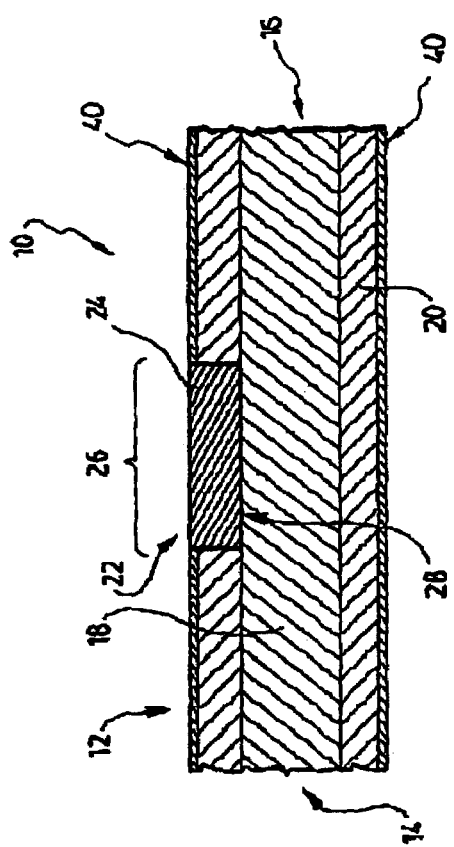
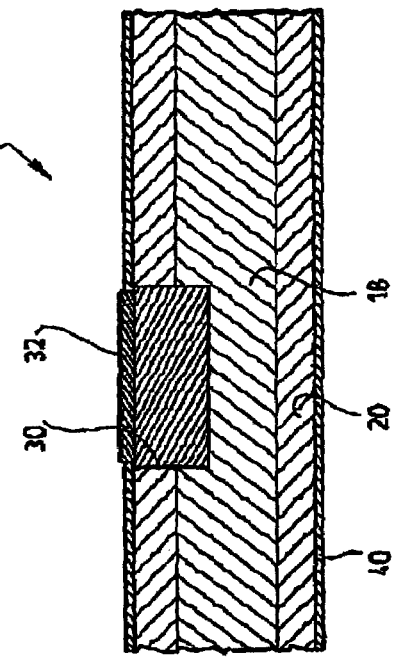

PACKAGED OPTICAL SENSORS ON THE SIDE OF OPTICAL FIBERS

FIELD OF THE INVENTION

The present invention generally relates to optical fibers, and more particularly concerns an optical fiber sensor integrated on a preferred azimuthal portion of the side of an optical fiber. An exemplary application of this invention is a temperature measurement in vivo.

BACKGROUND OF THE INVENTION

Optical fiber sensors are well known and their application fields cover a broad area ranging from physical parameter measurement to chemical and biochemical parameter measurement.

Patents and scientific papers have also been published in the field of chemical and biochemical measurement through luminescent optical fiber sensors. These cover the biomedical field through the measurement of physiological parameters such as pH, $O_2$, glucose, and $CO_2$ concentration in blood.

Another major area involved by the luminescent detection through optical fiber sensors is the biomedical diagnostic domain through optical biopsy. This area involves the evaluation of biological tissues through the measurement of a tissue's auto-fluorescence or through induced fluorescence by specific markers revealing the presence or absence of pathological tissues. These techniques are currently under development but some have reached the clinical level.

Of particular interest is the measurement of temperature through luminescent optical fiber sensors since optical fibers, unlike thermistors and thermocouples, are not affected by microwaves used in thermal treatment of cancers.

Luminescent optical fiber sensors usually work as follows: an excitation wavelength is directed into the optical fiber entrance with appropriate optical components. The excitation light travels through the fiber up to the other end of the fiber, where a luminescent material has been packaged at the fiber tip. The incoming light excites the luminescent material which in turn emits its luminescent light. The material is chosen such that its luminescent light properties (intensity, spectral content, lifetime decay) vary with the parameter to be measured. The luminescent light follows the optical fiber path down to the fiber entrance and is then collected and filtered against the excitation wavelength with proper optics and electronics. Finally, the luminescent properties of the collected light are analysed to deduce the parameter value to be measured.

Most or all of these luminescent optical fiber sensors are packaged at one end of the fiber. Thus, few or none allow distributed measurements, either by spatially distributing the measurement of one parameter or through simultaneous measurement of many parameters, through only one fiber. Furthermore, in some cases, the fact that the sensor is placed at the end of the fiber renders its use less attractive.

For example, it is known that the temperature measurement of intra-arterial walls can be used as a diagnostic tool to detect active arteriosclerotic plaque at risk of disrupting. These active plaques have a temperature which is higher (from 0.1 to 1.5° C.) than normal arterial walls, and the temperature measurement of intra-arterial walls can then be used to detect these plaques. If one measures the temperature of intra-arterial walls with a luminescent optical fiber temperature sensor placed at the end of the fiber, one will use the small and potentially piercing sensing end of the fiber to make contact with the arterial wall. This is a serious disadvantage, since one can accidentally pierce the artery or worse, the active arterial plaque can be broken, which can result in a cardiac stroke.

The same configuration, i.e. the use of the sensor at one end of the fiber, could be used to measure the fluorescence coming from the arterial wall. In this case, the optical fiber is used as a light pipe to make the excitation light reach the arterial wall and to gather part of the luminescent light from the wall and guide it down to the fiber entrance. The luminescent light can then be analysed to identify the type of biological tissue and eventually diagnose the presence of plaques at risk of disrupting. However, to excite and collect the maximum of light level, one needs to put the fiber end in contact with the arterial wall, which can lead to the problems described above. This is also true for any optical fiber extrinsic spectroscopic sensor which collect light (luminescent or not) from biological tissue or from an optical sensing material making contact with that tissue.

Thus the use of conventional optical fiber sensor packaged at one end of the fiber should be prohibited in cases where biological tissue damage can cause health problems.

Therefore, there is a need for a sensor better adapted for a safe in vivo spectroscopy. Moreover, it would be desirable to provide a sensor offering more precise measurement.

SUMMARY OF THE INVENTION

It is an object of the present invention to provide an optical sensor on a preferred azimuthal portion of the side of an optical fiber.

In accordance with the invention, this object is achieved with an optical sensor including an optical fiber for conveying a light beam. The optical fiber is provided with a first end for receiving the light beam and a second end opposed thereto, a core and a cladding surrounding the core. The optical fiber also includes at least one claddingless portion having a longitudinal, a radial and an azimuthal extent. Each of the claddingless portions defines a shaped cavity extending in the optical fiber between the two opposite ends. The optical sensor further includes a sensing material extending in each of the cavities for forming a sensing area therein in contact relationship with the core.

It is a preferable object of the present invention to provide a sensor well adapted for spectroscopic measurement in the biomedical and biotechnological fields.

Accordingly, there is provided an optical sensor wherein the optical fiber has a predetermined permanent shape for projecting the sensing area outwardly, thereby allowing a safe use of the optical sensor for in vivo measurement. This also allows a better contact of the sensor with the area to be sensed.

According to another aspect of the present invention, there is provided an optical sensor having a plurality of sensing areas separated to each others by a predetermined distance. In a preferred embodiment, each of the sensing area extends in a longitudinal alignment relationship with each others. In another preferred embodiment, each of the sensing area extends in an azimuthal alignment relationship with each others.

According to yet another aspect of the present invention, there is provided an optical sensor wherein the sensing material can be either a luminescent material either a transparent material.

It is another object of the present invention to provide an optical sensing system including at least one optical sensor.

Each of the optical sensors is provided with an optical fiber for conveying a light beam. The optical fiber has a first end for receiving the light beam and a second end opposed thereto, a core and a cladding surrounding the core, and at least one claddingless portion having a longitudinal and a radial extent. Each of the claddingless portions defines a shaped cavity extending in the optical fiber between the two opposite ends. The optical sensor further includes a sensing material extending in each of the cavities for forming a sensing area therein in contact relationship with the core. The optical sensing system also includes a light source for injecting light into the first end of the optical fiber of each of the optical sensors. The system also includes a detector operatively connected to one of the ends of the optical fiber of each of the optical sensors for detecting light coming from each of the sensing areas. The system is further provided with an analyser operatively connected to the detector for analysing light coming from each of the sensing areas.

It is a preferable object of the present invention to provide an optical sensing system for temperature measurement.

BRIEF DESCRIPTION OF DRAWINGS

The present invention and its advantages will be more easily understood after reading the following non-restrictive description of preferred embodiments thereof, made with reference to the following drawings in which:

FIG. 1a is a schematic cross sectional side view of an optical sensor according to a preferred embodiment of the present invention.

FIG. 1b is a cross sectional front view of the optical sensor of FIG. 1a.

FIG. 2 is a schematic cross sectional side view of another optical sensor according to another preferred embodiment of the present invention;

FIG. 7b is a cross sectional side view of the fiber of FIG. 7a.

Figure 3A:
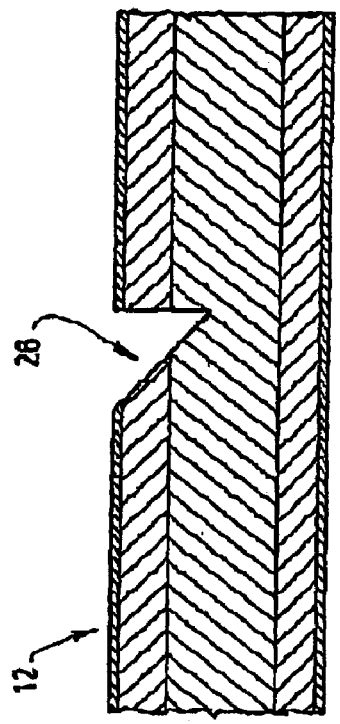
FIGS. 3a to 3h are schematic cross sectional side views of different optical sensors according to different preferred embodiments of the present invention; each of the optical sensors having a portion of its cladding and of its core removed with different shapes.

While the invention will be described in conjunction with an example embodiment, it will be understood that it is not intended to limit the scope of the invention to such embodiment. On the contrary, it is intended to cover all alternatives, modifications and equivalents as may be included as defined by the appended claims.

DESCRIPTION OF A PREFERRED EMBODIMENT

As mentioned previously, the present invention relates to optical fiber sensors and more particularly to optical fiber sensors packaged on the side of optical fibers. The application domain covers a large area but mainly aims the field of luminescent and spectroscopic optical fiber sensors with application possibilities in the field of telecommunications.

More specifically, the packaged sensor application field aims the measurement of temperature and the spectroscopic measurement in the biomedical and biotechnological domains.

The spectroscopic sensors cover the identification and concentration measurement of biological, biochemical and chemical compounds aiming applications in the biomedical, biotechnological, chemical, environmental and industrial domains. More specifically, the concentration measurement of pH, $O_2$, $CO_2$, and glucose are of interest. Identification of biological pathologic tissues through spectroscopy is more specifically aimed.

The present invention alleviates the most glaring problem of the prior art, viz. the placement of the sensor at the tip of a fiber, since the sensing material is placed on one side of the fiber. The sensing material could then make a gentle contact with the surface to be measured through the side of the fiber, which is not as piercing as its tip. Thus, this will prevent the fiber from damaging for example, the arterial wall in the example described above.

The present invention concerns the placement, in the side of an optical fiber or any other appropriate waveguide, of a sensing material. Referring to FIGS. 1a and 1b, there is shown an optical sensor 10 including an optical fiber 12 for conveying a light beam. The optical fiber 12 is provided with a first end 14 for receiving the light beam and a second end 16 opposed thereto, a core 18 and a cladding 20 surrounding the core 18. The optical fiber 12 is also provided with at least one claddingless portion 22 having a longitudinal, a radial and an azimuthal extent. Each of the at least one claddingless portion 22 defines a shaped cavity 28 extending in the optical fiber 12 between the two opposite ends 14, 16. The optical sensor 10 further includes a sensing material 24 extending in each of the cavities 28 for forming a sensing area 26 therein in contact relationship with the core 18.

The claddingless portion 22 is obtained by removing a longitudinal, a radial and an azimuthal part of the optical fiber 12. In the preferred embodiment illustrated in FIGS. 1a and 1b, the sensing material 24 does not penetrate into the core 18 of the optical fiber 12, but make an optical contact with it. Alternatively, according to another preferred embodiment of the present invention illustrated in FIG. 2, the shaped cavity 28 partially extends in the core 18 of the optical fiber 12. Thus, the sensing material 24 also extends in the core 18. Such an embodiment could advantageously be used if a greater coupling of light is required, as further described below. Moreover, the optical sensor 10 presented in FIGS. 1 and 2 may further include a thermally conductive material 30 surrounding the sensing material 24. In other words, the sensing material 24 can be further encased in a thermally conductive material 30, thereby increasing the sensitivity of the sensor 10.

The sensing material extending in the cavity 28 of the optical fiber 12 can be a luminescent material or can also be a transparent material. It is to be understood that throughout the present description, the expression "sensing material" is intended to specifically cover such materials as well as absorbing, reflecting or semi-transparent materials, or even any sensing material that is able to change properties of light reaching it. For example, according to a particular application, the sensing material may be chosen to have spectral properties changing with the presence and/or the concentration of chemical or biochemical compounds.

One can use a transparent material in order to make a window on the side of the fiber. This window can then transmit an excitation light from the fiber entrance to a luminescent material or a biological tissue and the luminescent light from the material or tissue back to the fiber entrance. The collected luminescent light can then be analysed to measure different desired parameters. In the case one uses a transparent material, such a transparent material preferably has an index of refraction which is greater than or equal to that of the core of the fiber. The window can also be used to transmit light having a wide spectral range to biological tissue or chemical compounds. The collected light could then be analysed to measure its spectral content and to deduce physical or chemical properties of the reflecting compounds or tissues.

Figure 4:
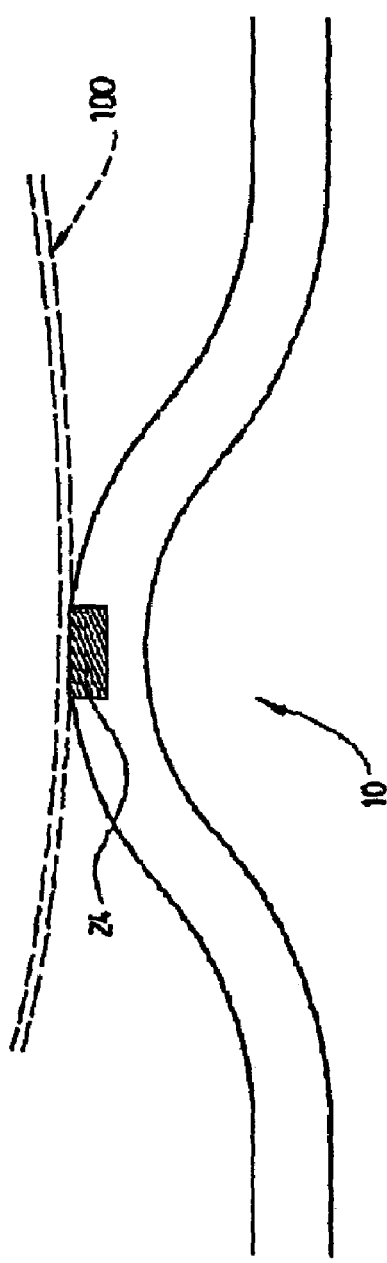
FIG. 4 is a side view of a permanently deformed fiber provided with an optical sensor according to another preferred embodiment of the present invention.
Figure 7B:
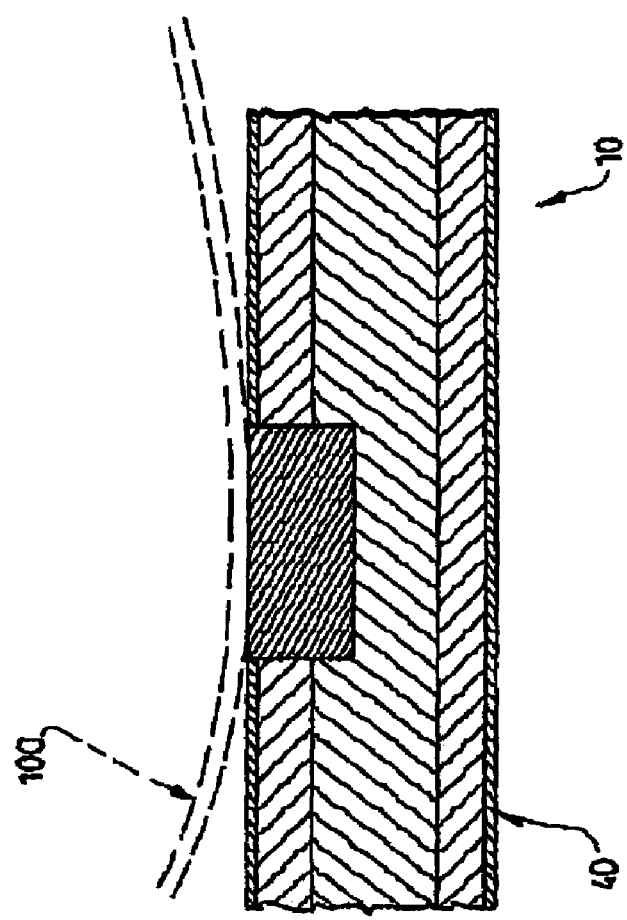
Figure 7A:
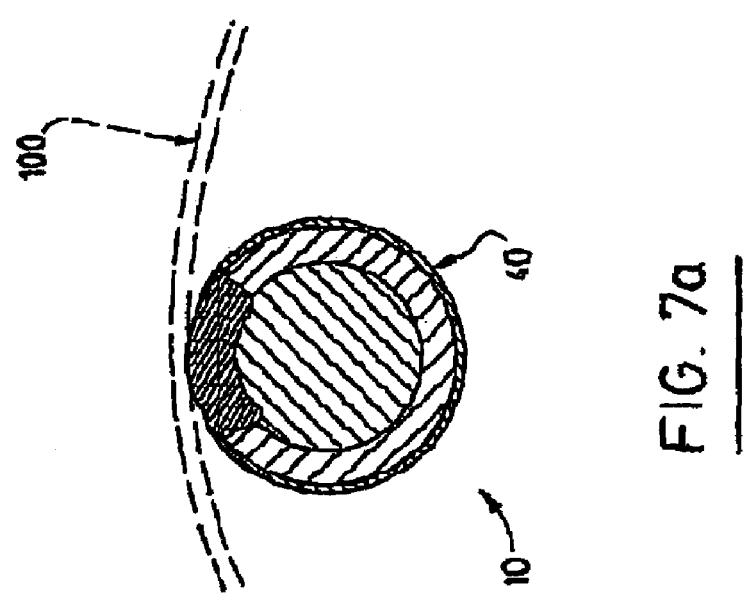
FIG. 7a is a cross-sectional front view of an optical sensor in contact relationship with an arterial wall according to another preferred embodiment of the present invention.

Referring now to FIGS. 4 and 7, a preferred application of such a sensor is temperature measurement. In order to discriminate between ambient temperature (i.e. the temperature around the fiber) and the actual temperature of the target which can, for example, be an arterial wall 100, it is preferable that the sensing material be placed only on one side of a preferred azimuthal portion of the side of the optical fiber, and that it covers only a part of the periphery of the fiber, as can be better seen on FIG. 7a. This is what is meant by the expression "longitudinal and radial" used in the present description. This also increases the sensitivity of the sensor of the present invention. The longitudinal extent of the sensing area will be determined by the application requirements. If the spatial resolution is an important issue, then this length should be small. If it is more an average value over a larger area which is of interest, then the length of the sensing area could be larger. In the case of the temperature measurement of arterial walls, this length should preferably be between 0,5 and 5 mm. The same type of approach can be applied to other preferred embodiments like concentration measurements or identification from spectral analysis.

From a theoretical point of view, it is known that the light rays going through an optical fiber core have an angular content comprised between rays going parallel along the fiber and rays reflected on the fiber core walls at a determined angle known as the critical total internal reflection angle ($\theta_c$). This critical angle is determined by the following relation:

$$\theta_c = \sin^{-1}(n_2/n_1) \qquad \text{Equation 1}$$

where $n_1$ and $n_2$ are the refractive indexes of the fiber core 18 and cladding 20 respectively. This angle is measured between a ray of light and the normal to fiber core walls. Rays having angle equal to or above this value ($\theta_c$) will be reflected on the fiber core wall and the ones having angle lower than this value will partly go through the wall. If one is to get light going to the sensing area without being totally reflected, he should either allow the light to hit the sensing area at an angle lower than this critical angle ($\theta_c$) or to choose the refractive index of the sensing material in order to change this critical angle, or both.

To get fiber core rays of light hitting the sensing area at an angle lower than the critical angle ($\theta_c$), one can shape the sensing area in order to lower the angle of rays hitting it, as illustrated in FIGS. 3a to 3h. Thus, to get the maximum amount of light reaching the sensing area, some preferred embodiments about the shape of the sensing area will follow this assumption. The preferred embodiment about the making of optical fiber having a sensing area on a preferred azimuthal portion of their side is to remove a lateral portion of the side of the fiber and replace it with the appropriate sensing material. This can be used to shape the sensing area of the fiber by removing the material on the side of the fiber and giving it the proper shape.

Figure 3B:
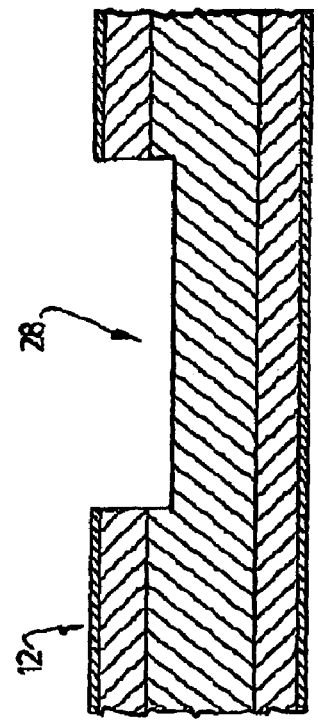
Figure 3C:
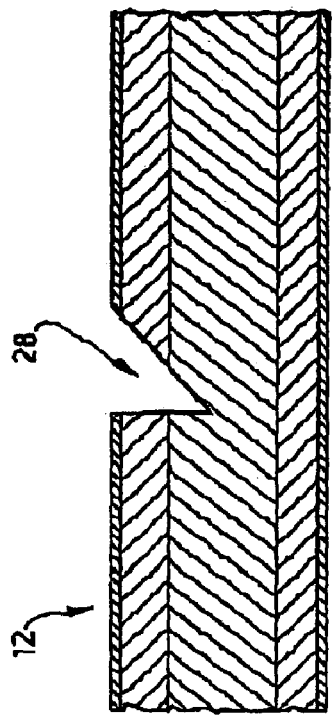

The shape of the removed part of the fiber is advantageously adapted to the application in order to get the optimum amount of light coupled from the fiber core to the sensing area and from the sensing area back to the fiber core. FIGS. 3a to 3h illustrate some of the preferred embodiments related to the shape of the removed part when it is made to reach the fiber core. The proper choice of the shape and extent of the removed part will depend on several parameters such as the particular application, the sensing parameters and material, the sensitivity or amount of light available from and back to the fiber core, etc, . . . . For example, if one is to sense the temperature on a very small portion of a surface, the embodiments represented through FIGS. 3a, 3b, and 3c are better choice than embodiments represented by FIGS. 3d, 3e and 3f which are more convenient for measurement over large area or average value measurements.

Figure 3D:
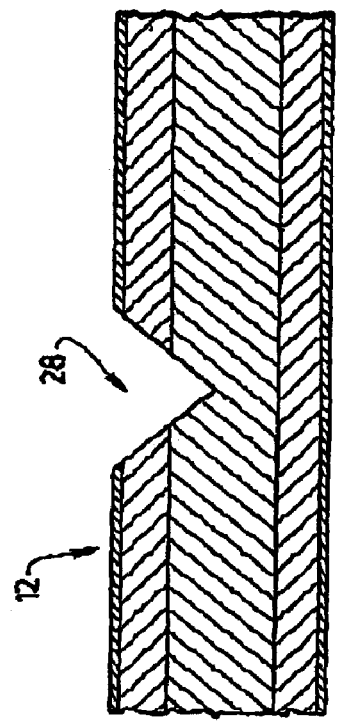
Figure 3F:
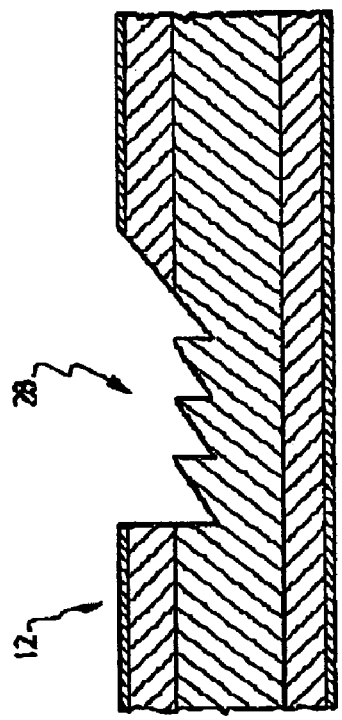
Figure 3H:
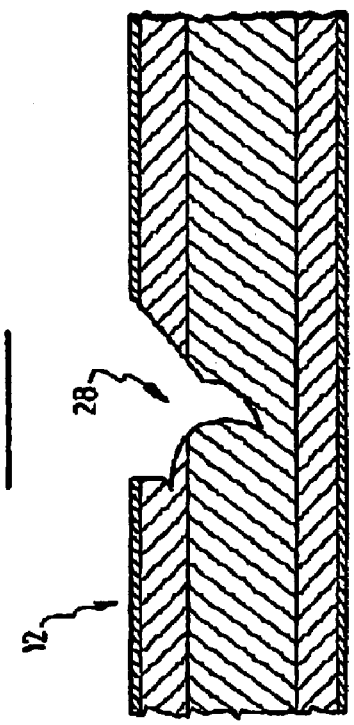
Figure 3E:
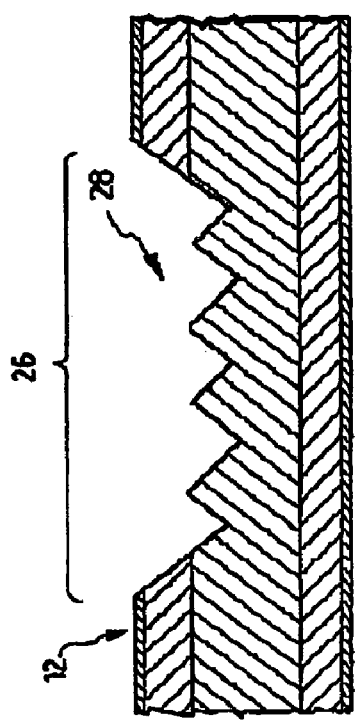
Figure 3G:
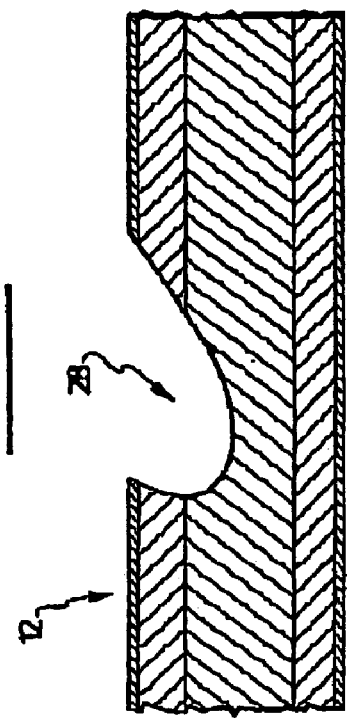

If the sensing material extending in the shaped cavity 28 of the fiber 12, has a refractive index ($n_3$) equal to or less than the refractive index of the cladding ($n_2$), then the amount of light coupled from the fiber core to the sensing area will be the same for embodiments illustrated by FIGS. 3a and 3d. This comes from the fact that only the portion of the sensing area 28 facing the light will allow the coupling of the light. The flat portion parallel to the fiber wall in FIG. 3d will couple very little light since it will act identically to the fiber wall except for residual absorption of evanescent waves into the luminescent material. In this case, to increase the coupling of light to a greater extent of the sensing area 28, embodiments illustrated on FIG. 3e, 3f or 3h are preferably used.

On the other hand, if the sensing material extending in the shaped cavity 28 of the fiber 12, has a refractive index ($n_3$) greater than the refractive index of the fiber core ($n_1$), the light will more easily couple from the fiber core to the sensing material, but could suffer total internal reflection when going from the sensing material back to the fiber core. This will make coupling from the sensing material to the fiber core less efficient for embodiment illustrated by FIG. 3d and again embodiments represented by FIGS. 3e and 3f could be useful to increase the coupling efficiency. Embodiment illustrated in FIG. 3g could also be used, then acting like a lens and increasing the coupling efficiency in and out the sensing material. If a very large extent of the sensing area is needed, many lens-like shapes like FIG. 3g could be placed beside one another similarly to triangle-like shape of FIGS. 3e and 3f to increase coupling efficiency. Of course, any other convenient shape of the cavity 28 could also be envisaged, according to a specific application.

To form the cavity 28, the removal of the portion of the fiber can be done by a chemical etching process or by laser processing, preferably a laser ablation. The chemical etching process could be done through masking of the fiber except for the part to be etched. The masked fiber is then exposed to HF that dissolves the glass and shape the fiber in a rather linear way by removing progressively the exposed glass. This can be used to create square-like shaped cavity 28, as illustrated on FIG. 3*d*. However, this can hardly be used to shape the fiber side with irregular shapes like embodiments illustrated on FIGS. 3*a*; 3*b*, 3*c*, 3*e*, 3*f*, 3*g* and 3*h*. In these cases, the preferred technique to get irregular shapes is laser ablation. This technique can be used to obtain complex and precise shapes for the cavity 28, ranging in size from few microns to many hundreds microns and even millimetres. Furthermore, laser ablation offers a better flexibility over chemical etching of fibers and probably ensure a better mechanical and physical integrity of the fiber core.

The integration of the sensing material in the shaped cavity of the fiber can be done in many ways. In the case where the sensing material is in the form of a powder, it can be inserted by integrating it with an epoxy glue, preferably having a high thermal conductivity coefficient if the sensor is to be a temperature sensor. The sensing material could also be integrated into a silica powder which can be melted into the opening by heating it with a laser. In the case where the sensing material can be melted with a laser without losing its sensing properties, it could be directly melted into the opening. Yet alternatively, the sensing material can be included into a paste, which can be cured by UV or laser illumination. In the case where the sensing material can not be down sized to a powder or a paste, it can be chemically etched or laser machined to match the shape of the cavity 28 of the fiber. This sensing part can then be glued in place with epoxy for example or joined to the fiber with a melting material placed between the sensing material and the shaped cavity of the fiber, and then heated in an oven or with a laser beam to complete the joining process. These techniques could be used as well for many types of sensing materials such as, for example, but not limited to, luminescent, absorbing, non-linear, transparent, polarizing, porous, sol-gel or even birefringent materials.

As previously said and according to Equation 1, in order to obtain better results, the coupling of the light from the optical fiber core to the sensing area can be optimized through the proper choice of the sensing area shape and/or of its refractive index with respect to the one of the fiber core. This could be achieved by making the refractive index of the sensing material higher than the refractive index of the fiber core by a proper choice of the sensing material or by including a material with a refractive index significantly higher than the one of the fiber core to the sensing material.

In the case where the shaped cavity of the fiber does not extend in the fiber core, as illustrated in FIG. 1, one has no choice but to use a sensing material having a refractive index higher than the one of the fiber core. However, this can be false if the sensing material can absorb part of the light coming from the fiber core. In this case, the absorption by the sensing material could be enough to couple a sufficient amount of light from the fiber to the sensing area.

Advantageously, a fiber with a core occupying a greater proportion of the section of the fiber is used. This reduces the risk of compromising the mechanical integrity of the fiber, since less material needs to be removed to reach the core. Furthermore, the manufacture of the sensor is simplified, since it is not necessary to penetrate deeply into the fiber. Another advantage is that the sensing material will be located closer to the surface of the fiber, which will promote a better reading of the parameter to be sensed (e.g. temperature), since the contact point will be less affected by the ambient environment (or average temperature) of the fiber. This could also lead to a faster response of the sensing element to sensed parameter (or temperature) change. Finally, the core of the fiber being greater, it will be easier to couple light from the sensing material back into the fiber core. For example, a fiber having a total diameter of 125 µm having a core diameter of 100 µm (a standard multimode fiber) requires the removal of 13 to 25 µm. However, in the case of luminescent intensity time decay measuring techniques, a fiber having a greater core has a high modal dispersion, which can negatively impact on the measurements if luminescent lifetime decay of the order of a nanosecond is used. A fiber having a core of 100 µm and an index jump of 0.015 has a modal dispersion estimated to be 0.05 ns/m. Obviously, a monomode fiber or any convenient waveguide could also be envisaged, according to a particular application.

Figure 5A:
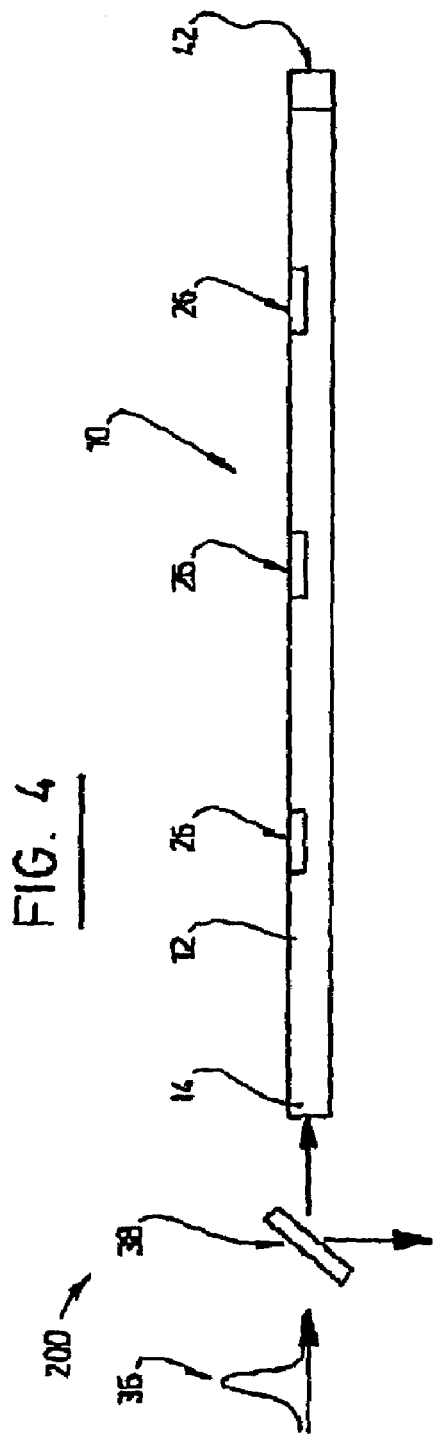
FIG. 5a is a schematic representation of an optical fiber provided with a plurality of sensors longitudinally arranged thereon according to another preferred embodiment of the present invention.
Figure 5B:
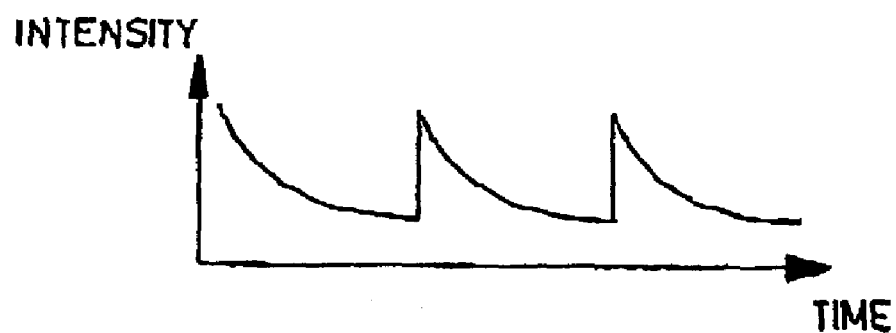
FIG. 5b is a graph illustrating an optical technique known as Optical Time Domain Reflectometry.

According to another object of the present invention and with reference to FIG. 5, there is also provided an optical sensing system 200 including at least one optical sensor 10 provided in an optical fiber 12, as previously described. The optical sensing system includes a light source for injecting light 36 into the first end 14 of the optical fiber 12 of each of the optical sensors 10. A detector 38 operatively connected to one of the ends of the optical fiber 12 of each of the optical sensors 10 is also provided for detecting light coming from each of the sensing areas 26. Such an optical sensing system finally includes an analyser operatively connected to the detector for analysing light coming from each of the sensing areas. In a preferred application which will be described in more details below, such a system is used as a temperature sensing system.

Thus, in order to measure a parameter with a sensor made according to the present invention, such as temperature, a sensing light is directed into the optical fiber entrance with appropriate optical components. The sensing light travels through the fiber up to the area where the sensing material has been packaged. The sensing light reaches the sensing material which in turn modifies its optical properties. The sensing material is chosen such that its optical properties (luminescence, intensity, spectral properties, absorption, reflection, lifetime decay, ...) vary with the parameter to be measured in a well known manner. The returned light is collected and filtered against the sensing light with proper optics and electronics. Finally, the optical properties of the collected light are analysed to deduce the parameter values to be measured.

In some cases, care must be taken to minimise the light reaching the area to be sensed through the sensing material, which could cause a parasitic signal induced on the area to be sensed. This can be obtained by deposing an opaque or reflecting film 32 above the sensing material 24, as illustrated in FIG. 2. However, in the cases where this parasitic signal must be measured as the sensing signal, such as auto-fluorescence of biological material, the sensing material and its substrate can be a transparent material having an index of refraction equal to or greater than the one of the fiber core. Thus, the light reaching this transparent material will have a tendency to exit the core of the fiber to reach the area to be sensed. In one of the preferred applications which is the measurement of temperature of intra-arterial walls, it is also contemplated to use this technique, combined with a thermally conducting luminescent material 40 coated on the surface of the fiber 12 to increase the capability of the sensor 10 to discriminate between the sensed area (e.g. the arterial walls) temperature and the ambient temperature (e.g. the blood temperature).

Figure 8A:
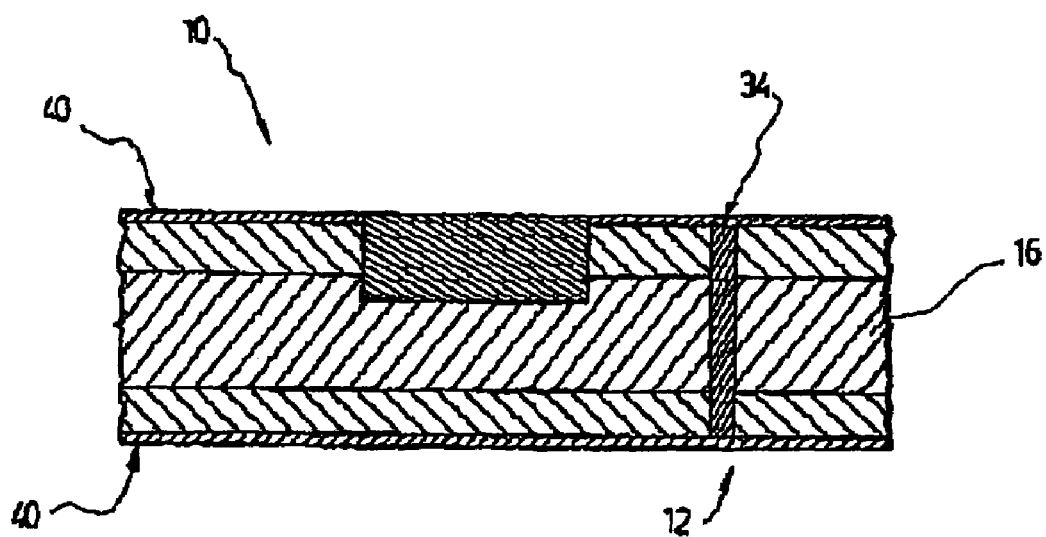
FIG. 8a is a schematic cross sectional side view of a fiber including a reflection splice proximate the sensor and extending perpendicularly to the fiber optical axis.
Figure 8B:
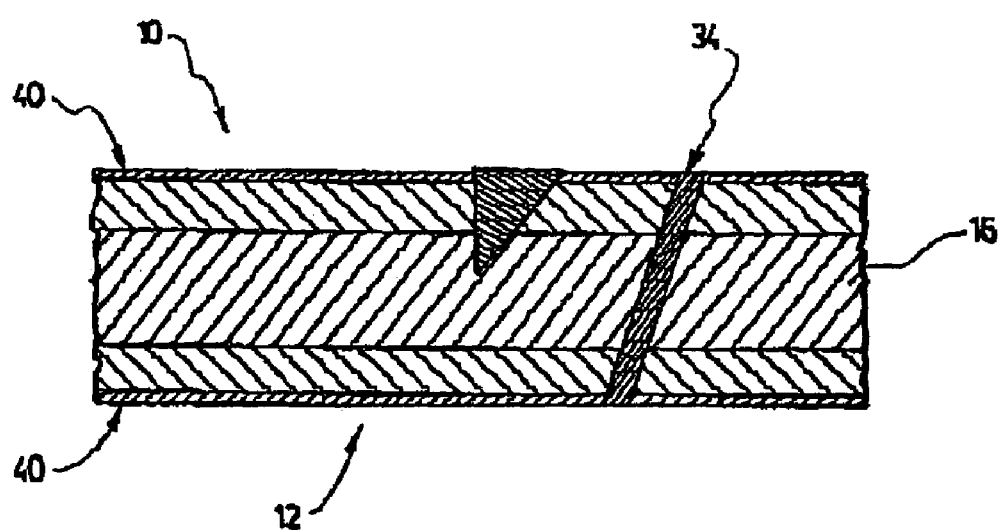
FIG. 8b is a schematic cross sectional side view of a fiber including a reflection splice proximate the sensor and extending with an angle with respect to the fiber optical axis.

Referring now to FIGS. 8a and 8b, the optical sensor 10 may be further provided with a reflector 34 extending radially inside the optical fiber 12 between the sensing area 26 and the second end 16 of the optical fiber 12, in the vicinity of the sensing area 26.

The presence of a reflector 34 near the sensing material allows maximizing the return of the luminescent light towards the excitation source. This can be done by placing on a section of the fiber a reflecting material such as, for example $TiO_2$. The proximity of this reflector 34 is important in order to minimise the temporal shift induced by differences in optical path produced between the sensing signal directly reaching the sensing material and the one produced by reflection, and also between the signal coming from the sensing material directly towards the source and the one reaching it after reflection. It is even more advantageous to place the reflector 34 at an angle in order to collect more light, as illustrated in FIG. 8b. The use of a fiber Bragg grating reflecting only the wavelength from the sensing material back to the entrance could be a better choice in the case where there is a sufficient amount of sensing light from the source. The fiber Bragg grating could be scribed into the fiber core by conventional UV scribing techniques or it could be scribed on the fiber surface by laser micro-machining of the cladding down to the fiber core, as well known in the art.

It should be noted that the use of the reflector 34 is optional, but preferable in order to increase the sensing light back to the entrance of the optical fiber. In some applications, it is also possible to inject light at one end of the fiber, to detect the parameter to be sensed at an intermediate position, and to detect the sensing signal at the other end of the fiber. In the case where the opposite end of the fiber is nor used and is not provided with a reflector, it is preferable to place an absorbent material or an index-matching material 42 (as illustrated in FIG. 5) in order to minimise the reflection of sensing light towards the sensor, and towards the input of the fiber. Furthermore, in the case of the preferred embodiment measuring temperature with a luminescent sensing material, if reflection is permitted, it should be as close as possible to the sensor in order to minimise a false reading of the lifetime decay of the luminescence.

Referring again to FIG. 5, there is shown an optical sensor 10, wherein the sensor includes a plurality of sensing areas 26 extending in line with each other. The sensing areas 26 are separated by a predetermined distance, and the measurements can be taken from each of the sensing areas 26 by a technique known as Optical Time Domain Reflectometry (OTDR).

Figure 6:
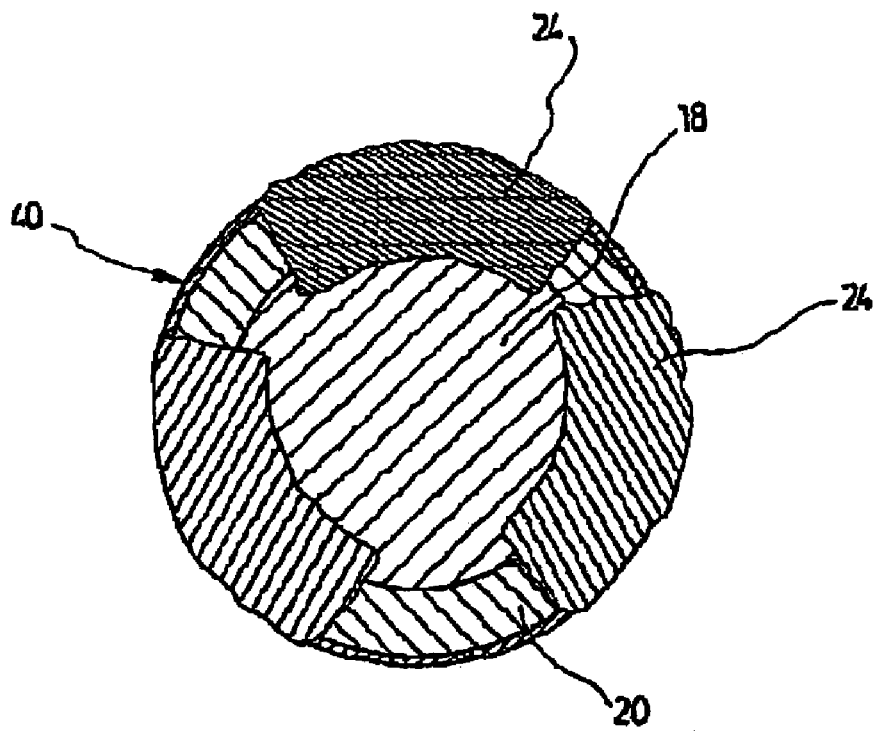
FIG. 6 is a cross-sectional front view of an optical fiber provided with a plurality of sensors azimuthally arranged thereon according to another preferred embodiment of the present invention.

Alternatively, referring now to FIG. 6, different sensing materials with sensing response at different wavelengths can advantageously be used, and these can be placed very close to each other, or even distributed on different azimuths of the fiber. In a preferred embodiment, each sensing area 26 extends in an azimuthal alignment relationship with each others around the optical fiber. The different sensing signals can then be distinguished through wavelength separation techniques, which are well known in the art and won't be further exposed therein.

Referring now to FIG. 4, there is shown an optical sensor which has been permanently deformed, for example by heating the fiber with a laser, in order to project the sensing area outwardly. This preferred embodiment is particularly advantageous for inner wall temperature measurement, since it insures that the sensing area remains in contact with the wall 100 for the duration of the measurement (as better shown in FIGS. 7a and 7b).

Although the optical sensing system according to the present invention has been described in details for the particular application of temperature measurement, it should be understood that such a sensing system could also be useful in many other applications such as, for non-restrictive example, the measurement of a pH concentration, $O_2$, $CO_2$ concentration or glucose concentration. Such a sensing system may also be used as a biological tissue identifying system. Moreover, although the present invention has been explained hereinabove by way of a preferred embodiment thereof, it should be pointed out that any modifications to this preferred embodiment within the scope of the appended claims is not deemed to alter or change the nature and scope of the present invention. More specifically, the present invention is not limited to temperature measurement, but can be used for any parameter measurement, in vivo or not, where small sensors are required, or where insensitivity to EM radiation is required (for example in nuclear reactors). Also specifically, the present invention is not limited to the use of luminescent sensing materials, but can use any sensing materials (such as absorbing, reflecting, transparent, semi-transparent, non-linear, porous, sol-gel, polarizing, electro-optical, birefringent, . . . materials) that change properties of light (such as wavelengths or spectral content, temporal properties, polarisation, relative intensity or power, . . . ) impingent on it through absorption, reflection, radiation (or emission), non-linear effects, guiding properties, . . . .

The invention claimed is:

1. An optical sensor comprising an optical fiber for conveying a light beam, said optical fiber being provided with a first end for receiving said light beam and a second end opposed thereto, a core and a cladding surrounding said core, said optical fiber having a longitudinal portion extending between said first and second ends having a predetermined longitudinally curved permanent shape and an intrinsic flexibility to allow a temporary deformation thereof, said optical fiber further having a claddingless portion having a longitudinal, a radial and an azimuthal limited extent, said azimuthal extent being less than 180 degrees, said claddingless portion defining a shaped cavity extending on said longitudinal portion so as to project outwardly there from, said optical sensor further comprising a sensing material extending in said cavity for forming a directional sensing area therein having a limited azimuthal extent less than 180 degrees in optical contact relationship with said core adapted to provide a directional selective contacting sensing, the longitudinally curved permanent shape and the intrinsic flexibility of the longitudinal portion, in combination with the directional sensing area projecting outwardly there from, enhancing contact between said directional sensing area and a sensed area of a solid surface, providing for discrimination between parameters of surrounding fluid and parameters of said sensed area to be measured.

2. The optical sensor according to claim 1, wherein said cavity extends radially inside said core.

3. The optical sensor according to claim 1, further comprising at least one additional claddingless portion, each of said claddingless portions defining a corresponding sensing area, each of said sensing areas extending in a longitudinal alignment relationship with other of said sensing areas, each of said sensing areas being separated from other of said sensing areas by a predetermined distance.

4. The optical sensor according to claim 1, further comprising at least one additional claddingless portion, each of said claddingless portions defining a corresponding sensing area, each of said sensing areas extending in an azimuthal alignment relationship with each other of said sensing areas around said optical fiber, each of said sensing areas being separated from other of said sensing areas by a predetermined distance.

5. The optical sensor according to claim 1, wherein said core has a refractive index, said sensing material has a refractive index greater than or equal to the refractive index of the core, said shaped cavity has a predetermined shape adapted to provide an increased coupling efficiency of light from the fiber core to the sensing area and from the sensing area back to the fiber core.

6. The optical sensor according to claim 1, wherein the sensing material is a luminescent material.

7. The optical sensor according to claim 1, wherein the sensing material has spectral optical properties sensitive to a concentration of a chemical or a biochemical compound.

8. The optical sensor according to claim 1, wherein the sensing material has spectral optical properties sensitive to a presence of a chemical or a biochemical compound.

9. The optical sensor according to claim 1, wherein the sensing material is a transparent material adapted to couple light out from the fiber core to the sensed area and from the sensed area back to the core to allow direct measurement of said parameters from spectroscopic or luminescent optical properties of said sensed area.

10. The optical sensor according to claim 1, further comprising a thermally conductive coating surrounding said sensing material and having a thermal conductivity higher than a thermal conductivity of said optical fiber.

11. The optical sensor according to claim 1, further comprising a reflecting film extending on said sensing material.

12. The optical sensor according to claim 1, wherein said cavity is formed by a chemical etching process.

13. The optical sensor according to claim 1, wherein said cavity is formed by laser processing.

14. The optical sensor according to claim 1, wherein said optical fiber is a multimode optical fiber.

15. The optical sensor according to claim 1, wherein the second end of the optical fiber is provided with an index matching material.

16. The optical sensor according to claim 1, further comprising a reflector extending radially inside said optical fiber between the sensing area and the second end of the optical fiber, said reflector extending close to the sensing area.

17. The optical sensor according to claim 16, wherein said reflector extends angularly inside said fiber.

18. The optical sensor according to claim 16, wherein said reflector is a fiber Bragg grating.

19. The optical sensor according to claim 1, wherein said predetermined longitudinally curved permanent shape of said longitudinal portion is obtained by laser heating.

20. An optical sensing system comprising:
at least one optical sensor, each comprising an optical fiber for conveying a light beam, said optical fiber being provided with a first end for receiving said light beam and a second end opposed thereto, a core and a cladding surrounding said core, said optical fiber having a longitudinal portion extending between said first and second ends having a predetermined longitudinally curved permanent shape and an intrinsic flexibility to allow a temporary deformation thereof, said optical fiber further having a claddingless portion having a longitudinal, a radial and an azimuthal limited extent, said azimuthal extent being less than 180 degrees said claddingless portion defining a shaped cavity extending on said longitudinal portion so as to project outwardly there from, said optical sensor further comprising a sensing material extending in said cavity for forming a directional sensing area therein having a limited azimuthal extent less than 180 degrees in optical contact relationship with said core adapted to provide a directional selective contacting sensing, the longitudinally curved permanent shape and the intrinsic flexibility of the longitudinal portion, in combination with the directional sensing area projecting outwardly there from, enhancing contact between said directional sensing area and a sensed area of a solid surface, providing for discrimination between parameters of surrounding fluid and parameters of said sensed area to be measured;
a light source for injecting light into the first end of the optical fiber of each of said at least one optical sensor;
a detector operatively connected to one of said ends of said optical fiber of each of said at least one optical sensor for detecting light coming from each sensing area; and
an analyser operatively connected to said detector for analysing light coming from each sensing area.

21. An optical sensing system according to claim 20, wherein said system is a temperature sensing system.

22. An optical sensing system according to claim 20, wherein said system is a pH concentration measuring system.

23. An optical sensing system according to claim 20, wherein said system is a O2 concentration measuring system.

24. An optical sensing system according to claim 20, wherein said system is a CO2 concentration measuring system.

25. An optical sensing system according to claim 20, wherein said system is a glucose concentration measuring system.

26. An optical sensing system according to claim 20, wherein said system is a biological tissue identifying system.

* * * * *